United States Patent [19]
Baker et al.

[11] Patent Number: 5,089,407
[45] Date of Patent: Feb. 18, 1992

[54] ENCAPSULATION OF BIOLOGICAL MATERIAL IN NON-IONIC POLYMER BEADS

[75] Inventors: Carol A. Baker; Albert A. Brooks, both of St. Louis; Robert Z. Greenley, Frontenac; Jay M. Henis, St. Louis, all of Mo.

[73] Assignee: Monsanto Company, St. Louis, Mo.

[21] Appl. No.: 438,655

[22] Filed: Nov. 17, 1989

Related U.S. Application Data

[63] Continuation of Ser. No. 131,965, Dec. 11, 1987, abandoned.

[51] Int. Cl.$^5$ .................. C12N 11/12; C12N 11/04; C07K 17/04; C07K 17/12
[52] U.S. Cl. ........................... 435/179; 435/178; 435/182; 530/813; 530/814; 530/817
[58] Field of Search ............. 435/174, 176, 177, 178, 435/179, 182; 530/813, 814, 817

[56] References Cited

U.S. PATENT DOCUMENTS

| | | | |
|---|---|---|---|
| 3,242,055 | 3/1966 | De Lucia | 435/176 |
| 3,928,143 | 12/1975 | Caughlin | 435/176 X |
| 4,025,391 | 5/1977 | Kawashima et al. | 195/68 |
| 4,266,029 | 5/1981 | Banner-Jorgenson | 435/176 |
| 4,617,271 | 10/1986 | Nambu | 435/182 |
| 4,668,512 | 5/1987 | Houtchens et al. | 435/94 |
| 4,675,292 | 6/1987 | Lewis et al. | 424/93 |
| 4,722,898 | 2/1988 | Errede et al. | 435/182 |

FOREIGN PATENT DOCUMENTS

138193 6/1987 Japan.
214841 7/1987 Japan.

OTHER PUBLICATIONS

Hashimoto et al., J. Jap. Sewage Works Assoc., vol. 23, 2/1986, pp. 16–22.
Suslow et al., Phytopathology, vol. 72, No. 2, 1982, pp. 199–206.
Smith et al., J. Econ. Entomol., vol. 71, No. 5, 10/1978, pp. 814–817.

*Primary Examiner*—David M. Naff
*Attorney, Agent, or Firm*—Stanley M. Tarter; James W. Williams, Jr.; James C. Bolding

[57] ABSTRACT

Biological materials such as enzymes, proteins and peptides are encapsulated by forming a mixture of the material and an aqueous non-ionic polymer solution, spraying the mixture into a circulating water-immiscible non-solvent for the polymer at a temperature sufficient to freeze the beads and drying the frozen beads to remove essentially all unbound water such as to provide a water content of about 1–2 weight percent. Suitable non-ionic polymers are poly(vinyl alcohol), polyvinylpyrollidone, dextran and derivatized cellulose. A densification agent such as alumina may be present in the polymer solution to enhance specific gravity of the beads formed. Encapsulated material such as microbes produced by this process provide useful agricultural agents which can be delivered to the market in a dormant state and suitable for delivery to soil or plant leaves. The beads can be applied dry, via a planting or an insecticide box, or wet via a spray nozzle.

23 Claims, 5 Drawing Sheets

ENCAPSULATION OF BIOLOGICAL MATERIAL IN NON-IONIC POLYMER BEADS

This is a continuation of application Ser. No. 07/131,965, filed Dec. 11, 1987, now abandoned.

The present invention relates to encapsulation of biological material. More particularly, the present invention relates to a method of encapsulating biological material such as microbes (bacteria as well as fungi) and proteins in a polymer matrix to enhance the use of the material as agricultural agents (e.g. herbicides, insecticides, etc.) or for some other purpose such as an immobilized catalyst.

The use of microbes as agricultural products has been hampered by the lack of an efficient delivery system for the microbes. A microbe in the fermenter is not "farm-ready". There must be a system for maintaining microbial activity from the fermenter to the farmer and the product must be in a form that is acceptable and useful to the farmer. This may require use in the soil or adhesion to leaf surfaces even through periods of rain.

Five major advantages of the present method for encapsulating microbes are: (1) very high recovery of viable active microbes following the encapsulation procedure; (2) the finished product leaves the microbe in a dormant state suitable for storage; (3) the encapsulated microbe formulation is a free-flowing material which can be utilized using standard equipment; (4) encapsulated microbes may be caused to adhere to leaf surfaces; and (5) the present method provides a means to deliver biological material which is subject to photo degradation and/or enzymatically unstable.

Unlike prior art methods such as the alginate bead method of Bashan, ("Alginate Beads as Synthetic Inoculant Carriers for Slow Release of Bacteria that Affect Plant Growth", *Applied & Environmental Microbiology* Vol 51, No. 5, pp 1089-1098, (1986)), no regrowth step is necessary since usually less than 1.5 logs of cells are lost during the encapsulation process. Since no regrowth step is necessary, the structure of the beads is controlled by the polymer and bead making process and not by the effects of the growing microbe. This results in a more uniform and predictable structure, and release profiles which may be determined by the polymeric composition and microstructure of the beads.

In the alginate bead method of Bashan, viable bacterial numbers dropped 3 to 4 logs when the beads were freeze-dried leaving at most $10^7$ cells/gm of beads. Following the present method, yields of $10^8$ to $10^9$ have been reached without yet reaching the limit of loading capacity. Microbial loadings of $10^{12}$ viable cells per gram of beads should be possible.

STATEMENT OF THE INVENTION

The present invention provides a method for encapsulation of biological material in which the biological material is admixed with an aqueous non-ionic polymer solution in which the polymer is present at a concentration of at least 3% w/v. Beads are formed by adding the above mixture dropwise into a water-immiscible non-solvent for the polymer maintained at a temperature sufficient to rapidly freeze the bead but not so low to cause freeze fracture of the polymer bead. The polymer beads containing the biological material are then dried to remove substantially all unbound water contained in the beads.

In one aspect the invention enables microbes to become useful agricultural agents. The polymeric beads of the present invention deliver the microbe to the market in a dormant state. Beads can be made which are suitable for delivery to the soil or plant leaves. In addition, the polymeric materials used are biodegradable and the beads can be applied either dry, via a planting or an insecticide box, or wet via a spray nozzle.

Water soluble non-ionic polymers having a solubility of at least 3% w/v and which are not detrimental to the microbe to be encapsulated can be used. By non-ionic polymer is meant a neutral polymer exhibiting substantially no net charge. Polymer concentrations between 5% and 15% are preferred. Suitable polymers include poly(vinyl alcohol) (PVOH), preferably in a M.W. range from about 10,000 to 125,000 and from 85-100% hydrolyzed; polyvinylpyrollidone (PVP), preferably in a M.W. range from about 10,000 to 360,000; dextran, preferably in a M.W. range from about 10,000 to 249,000 and various derivatized cellulose polymers such as hydroxypropylcellulose (HPC), preferably in a M.W. range of about 60,000 to 1,000,000.

Dry PVOH is not readily soluble in cold water, so PVOH beads do not dissolve although swelling and fragmentation can occur. The extent of swelling and fragmentation can be controlled by the molecular weight of the PVOH polymer used. Swelling and fragmentation of PVOH beads are reduced with increased PVOH molecular weight. Dry PVOH is solubilized by heating the aqueous PVOH mixture to a temperature above 80° C., preferably to the boiling point. Beads made with PVOH are substantially insoluble in water at temperatures below 40° C. The integrity of the PVOH beads (rate of a dissolution) can be decreased by blending other cold water soluble polymers, such as polyethylene glycol (PEG) with the PVOH. Beads made from PVP, derivatized cellulose and dextran dissolve when placed in cold or room temperature water.

FIG. 2 represents a typical PVOH bead in whole and in cross-section showing the sponge-like porous structure. FIG. 3 represents a typical (10% w/v) PVP bead. FIG. 4 represents a typical (10% w/v, 60,000 m.w.) HPC bead.

The molecular weight of the polymer affects the mechanical strength of the bead. In general, the strength of the bead increases with increasing molecular weight. For example, PVOH beads made from a mixture of various molecular weights but having an average molecular weight of 61,000 swell but fragment very little when added to water. Beads made from 25,000 molecular weight PVOH fragment quickly and dissolve in water. Molecular weights below about 10,000 cause the beads to be very friable. In general, an increase in the molecular weight of the PVOH utilized will decrease the fragmentation. The structural integrity effects can be utilized to alter the release of microbes from the bead matrix. For example, fragmentation of the beads results in quicker release of the biological material contained therein.

One of the unique aspects of the present invention is that the beads can be freeze-dried and retain their morphology. This is possible because the polymers used are water soluble at higher concentrations with lower viscosities than materials currently used for cell immobilization (agar, alginates, etc.). Hence, beads can be made with sufficient polymer (>3% w/v) so that the bead exhibits useful strength upon removal of water. For example, at concentrations of about 5% w/v of PVOH or PVPs viscosities are below 1000 centipoise (cps). Depending on the polymer and its molecular weight one can increase the polymer concentration to its solubility limit. However, in most cases there will be no useful increase in bead strength above 15% w/v and some of the higher molecular weight polymers are too viscous above this concentration to readily make beads.

Figure 3:
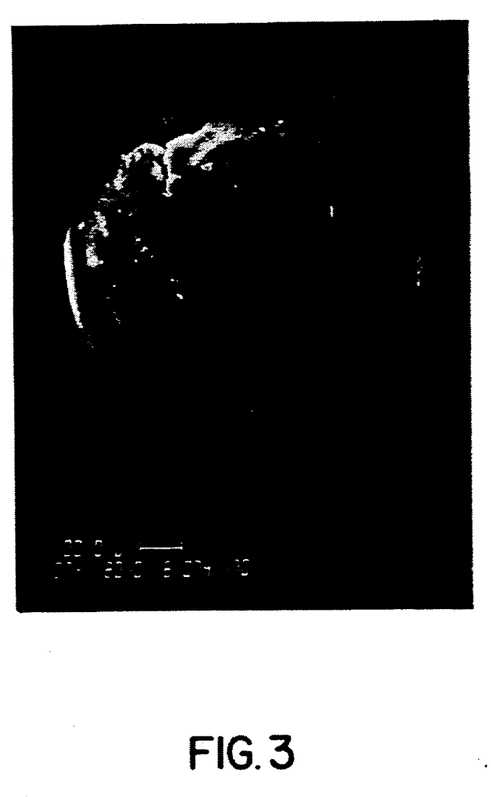
FIG. 3 represents a typical PVP bead.
Figure 4:
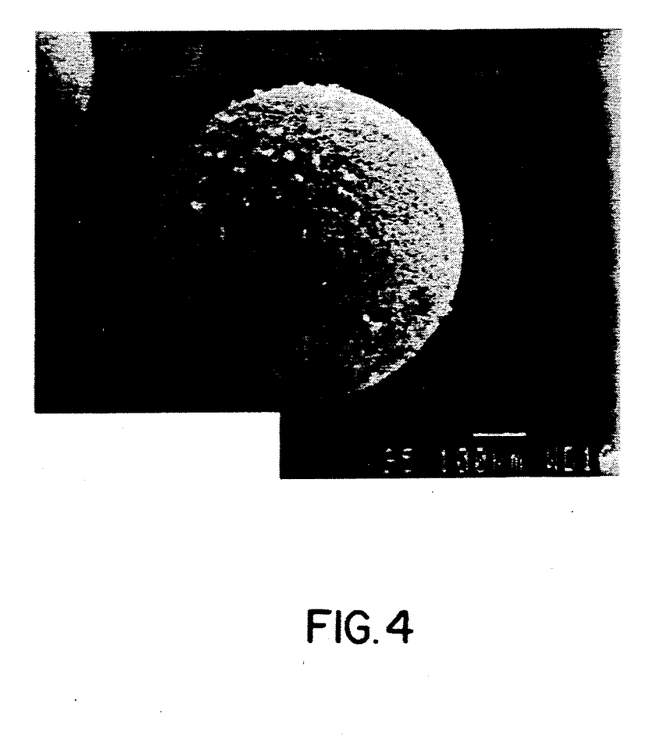
FIG. 4 represents a typical HPC bead.

Therefore, in another aspect the present invention provides useful compositions comprising a non-ionic water-soluble polymer and biological material, said composition being substantially free of unbound water and having a non-friable sponge-like porous structure. (See FIGS. 2-4)

In yet another embodiment, the present invention provides a solid composition which comprises a non-ionic polymer, which cannot be readily dissolved at temperatures below 80° C. but is dissolvable at temperatures above 80° C., and biological material, said composition substantially free of unbound water and substantially insoluble in water at temperatures below 40° C. In the cases where the biological material is a viable microbe, the microbe content may range between 0.01 and 50 wt % of the composition.

Polymer solutions can be autoclaved at 15 psig, 121° C. for 30 minutes. In many cases this is advantageous so that contamination by unwanted microbes can be avoided. Solutions are stirred while cooling to avoid "skinning" on the surface. The "skin" interferes with processing the solution into beads. Nutrients and/or densification agents can be added before autoclaving. Alternately, nutrients can be filter sterilized and added aseptically after autoclaving. Viscosity is preferably maintained in a range of 20 to 1000 cps. However, the only limitations on the viscosity are dictated by the method of bead making employed.

Since the pH of the polymer solution may change during autoclaving (e.g. acetate residues hydrolyzing from PVOH to form acetic acid in solution), it may be necessary to buffer the polymer solution to maintain a desired pH usually between 6-7.5. Buffers which may be used include any physiologically acceptable buffer which does not adversely affect the microbes. A preferred buffer is 0.05M sodium phosphate.

Addition of a densification agent is beneficial in most cases to enhance the specific gravity of the formulated bead to make them easier to handle. Any densification agent which does not adversely affect the activity of the microbe may be used. Suitable densification agents include silica, silica gel, bentonite and alumina. Alumina is particularly preferred. The alumina is mixed thoroughly with water and a sugar, such as dextrose or sucrose, before adding it to the polymer solution. This permits the alumina to be well dispersed and the sugar pretreats the alumina so that alumina interacts less with any hydroxyl groups on the polymer. This interaction of polymer and alumina can cause the solution to become stringy.

Gram positive and gram negative bacteria as well as fungi can be encapsulated using the method of the present invention. Exemplary microbes include *Bacillus thuringiensis;* microbes of the genus Pseudomonas such as *Pseudomonas fluorescens* identified by deposit number NRRL B-15132, NRRL B-15133, NRRL B-15134 and NRRL B-15135, ATCC 39802; microbes of the genus *Agrobacterium radiobacter* identified by deposit number ATCC 39803; and fungal species such as *Alternaria cassiae.* Microbes are added to the polymer solution after it is cooled to room temperature. Cells may be optionally washed of culture supernate although components normally found in culture media and cell products do not interfere with the preparation of the beads. In cases where the microbe may produce a detrimental metabolite, removal by washing is preferred prior to encapsulation. Cells are resuspended in a small amount of fluid prior to mixing with the polymer solution in order to obtain a uniform suspension. The suspending fluid can be simply the supernatant fluid (culture broth) from the initial centrifugation or it can be a specifically defined formulation to enhance the survival of a particular microbe during freezing and freeze drying. In addition, if there are adjuvants that will enhance the microbe's use as a herbicide or pesticide, or enhance its ability to colonize the target plant or soil, these agents may be added. In most cases the volume of suspension fluid is determined such that it is preferably not more than 5% of the polymer solution volume although it may be as high as 20% without difficulty.

Microbes are subject to injury from chilling, freezing and freeze-drying. Unfortunately, it is not fully understood what the injuries are, how these injuries occur, and how to prevent such injuries. Although it has been speculated that gram positive bacteria require less protection than gram negative bacteria, it is perhaps more likely that each microbe must be looked at as a special case. Included in the factors that must be considered are: age of the culture, rate of growth, type of growth medium, magnitude and rate of temperature drop, and the manner of growth following the cold stress. Addition of a sugar, skim milk, glycerol, dimethysulfoxide (DMSO) or other cryoprotective agents can stabilize the cultures. Different cryoprotective agents have different effects and their use is determined empirically. Glycerol, sucrose and DMSO have found wide applicability.

While the above considerations must be made for fungi as well, other treatments must also be made. During the encapsulation process fungal spores are exposed to large amounts of water. Since for a number of fungi the presence of water stimulates germination, it is preferred that the spores be pretreated to protect them from the water during the encapsulation process. It has been found that presoaking the spores in 6M sorbitol is an effective treatment. Spores pretreated with sorbitol in this manner do not wet as easily as untreated spores and survive the encapsulation process. Although pretreatment with sorbitol is preferred, pretreatment of fungal spores with polyethylene glycol (M.W. 200) also works.

Once the above mixture comprising the polymer and microbe or other biological material is complete, the mixture is added drop-wise to a cooling bath at about −30° C. The cooling bath is comprised of a liquid which is water immiscible and a non-solvent for the polymer. It is important that the liquid used in the cooling bath possesses both properties described above. Suitable non-solvents include hexane, petroleum ethers and Freon 113. Hexane is particularly preferred as a non-solvent.

The temperature is also an important parameter. If the temperature is too high (e.g. −15° C.) beads freeze more slowly and bead morphology is nonuniform. If the temperature is too low (e.g. −80° C.) the beads fracture as they form. The non-solvent is preferably stirred during the process to help with heat exchange and to allow large numbers of beads to be made rapidly without sticking together.

The criterion that the non-solvent also be water immiscible substantially prevents the non-solvent from penetrating the bead in concentrations high enough to be toxic to the microbes. In addition, bead formation does not readily occur with water miscible non-solvents since the polymer water mix disperses somewhat into the water miscible nonsolvent. This tends to result in the formation of stringy ropes of beads rather than discrete round beads.

Figure 1:
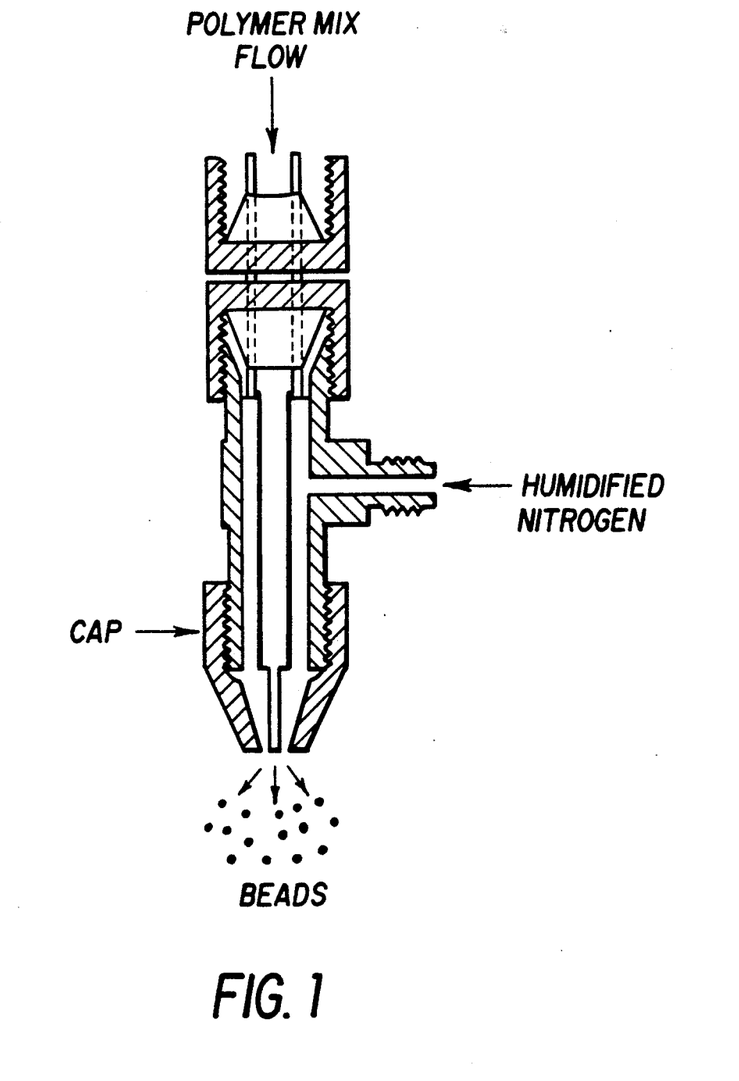
FIG. 1 represents a cross-sectional diagram of a nozzle useful in making beads.
Figure 2A:
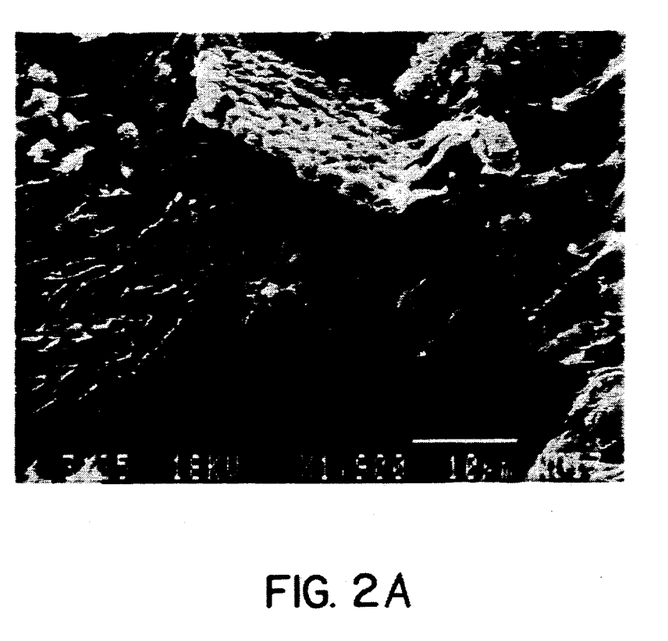
FIG. 2A is a photomicrograph of a cross-section of the PVOH bead depicted in FIG. 2B.
Figure 2B:
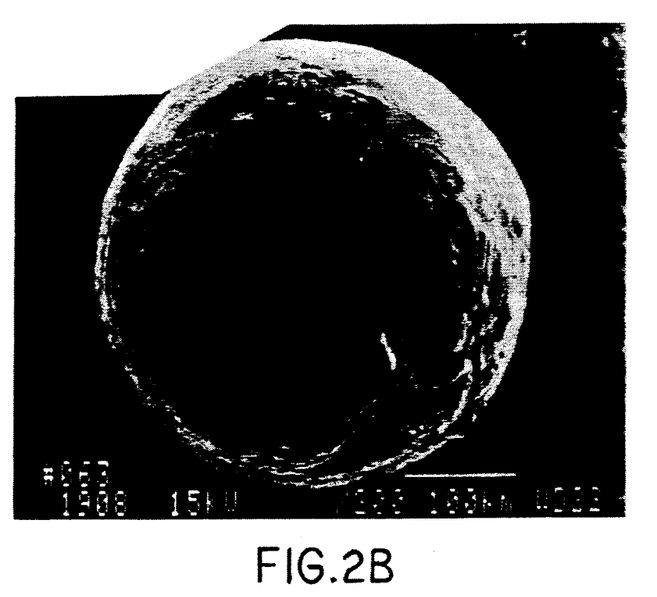

Any method for bead making that does not unduly diminish the viability of the microbe is suitable for use in the present method. FIG. 1 represents a nozzle which has been successfully used to make beads with no reduction in cell viability. Variations in the size of openings length of tubing, and the angle of the inside of the cap can be utilized, depending on the viscosities of the polymer/microbial mixture being sprayed and the size of the beads desired. A nozzle is connected to a reservoir of polymer mix which can be held at constant pressure. The pressure used also depends on the viscosity of the polymer mix and the size of beads desired. A sweep gas (preferably humidified nitrogen) enters above the tip and the flow rate is carefully controlled. Control of the sweep gas is vital to controlling bead size. The spray is collected in a chilled non-solvent bath at −30° C. The non-solvent temperature is maintained using a recirculating bath. Since this system involves no high pressure, large pressure drops, heat or ultrasonics to form the beads, it is very gentle to the cells. Substantially no cell damage occurs using this method therefore essentially no loss of viability results.

The frozen beads are collected from the cold non-solvent and dried. Although any means may be used to dry the beads, freeze-drying is preferred for cases in which retention of microbial viability is important. Upon collection from the non-solvent the beads are transferred cold to a freeze dryer. Drying the frozen beads takes from 8-48 hours depending on the configuration of the freeze dryer and the amount of beads to be dried. Incomplete drying results in clumping and loss of bead integrity. Over drying causes loss of viability. The beads are preferably freeze-dried until essentially all unbound water has been removed. In the cases of microbial encapsulation there will be about 1-2 wt % residual water in the dried bead.

The following examples are provided to more fully elucidate the practice of the present invention and are in no way intended to limit the scope of the invention.

Addition of Densification Agents

Beads can be formed with different densification agents, including, bentonite, silica, silica gel and alumina. Beads made with 10% w/v PVP plus 10% bentonite increased in density slightly from 0.09 g/ml (10% w/v PVP only) to 0.14 g/ml. Addition of more than 10% bentonite caused the viscosity to increase to a level where the difficulty of handling the more viscous solution outweighed the advantage in increased density of the final product. Silica can be added to at least 20% and at the 20% concentration density of the final product was approximately 0.25 g/ml. At these concentrations the silica did not increase the viscosity to unmanageable levels and was not toxic to the cells being encapsulated. Silica gels were added at the same concentration as the silica with similar results. However, the silica gels used were treated and it was found that the pH of the mixture of polymer, silica gel and cells was much lower. pH changes can adversely affect cells and/or proteins being encapsulated.

Due to its greater density, alumina causes a greater increase in bead density. The preferred type of alumina is alundum which is untreated and does not have a high surface area. Use of high surface area alumina decreased cell viable numbers by more than two logs. Alumina content to 30% may be used in both PVP and PVOH beads. Beads made with the 30% concentration had a density of approximately 1.8 g/ml and were easy to handle with good flow characteristics. Alumina particle sizes of 10 microns or less are preferred to assure good handling characteristics to the polymer mixes to provide good flow through bead making orifices without clogging. In all cases it was necessary to use high speed mixers or blenders to disperse the solids in the polymer solutions or to prewet the solids before addition.

Pretreatment of Alumina

Addition of alumina to poly(vinyl alcohol) solutions resulted in the solution becoming somewhat stringy. It is believed this is due to a coordination effect between the alumina which is capable of electron sharing and the hydroxyl groups on the PVOH. Beads were made by dissolving the polymer in ⅝ of the final amount of water. Five percent dextrose was then added to the remaining water and this solution was used to prewet the alumina. The hydroxyls in the dextrose interacted with the alumina which meant that the alumina interacted less with the polymer when it was combined with the prewet alumina. Sucrose was also used and worked equally well.

Stabilization of Microbes

The literature on freeze-drying bacteria has numerous references to the stabilization of bacteria during the freezing and freeze-drying process by means of additives, frequently sugars. In the present process addition of sucrose and dextrose to the polymer cell mixture prior to processing helped to stabilize the gram negative bacteria. Experiments on the encapsulation of *Pseudomonas fluorescens* show that if untreated cells are present at a concentration of $10^9$ per ml, then after encapsulation viability counts were $10^6$ cfu per ml. However, adding 1% glucose or sucrose to the mixture prior to encapsulation resulted in yields as high as $10^8$ cfu/ml from mixtures originally containing $10^9$ cfu/ml.

Encapsulation of the fungus *Alternaria cassiae*, was not successful until a pretreatment for the fungus was devised. Without pretreatment none of the conidia survived the freezing process. With the pretreatment 50% or more of the fungi survived the entire encapsulation procedure. The pretreatment consists of soaking the conidia in a 6 molar sorbitol solution for one to two hours prior to mixing the conidia with the polymer solution. When examined microscopically, spores that were pretreated did not appear to wet as readily as untreated spores. It is believed that the delayed wetting results in less damage to the conidia when freezing occurs. Pretreatment using polyethyleneglycol 200 also works.

Bead Making

A polymer mix was made consisting of 5% PVOH (78K MW), 1.5% PVOH (125K MW), 3.5% PVOH (10K MW), 0.1% protease peptone #3, 0.05M $Na_2HPO_4$ and 20% alumina. The viscosity of this mixture was 360 cps. Beads were made using the nozzle illustrated in FIG. 1. A reservoir containing the polymer mix was filled and placed under a pressure of 7 psig. Pressures of 2-15 psig have been used depending on the polymer used and size of beads desired. A valve is opened permitting the polymer to flow down to the tip. Sweep gas of humidified nitrogen is used to break up the polymer stream and form the beads. Flow of the sweep gas was 3 standard liters/minute (slpm). Beads were collected in hexane at $-30°$ to $-35°$ C. and then freeze-dried. Dried beads were screened and found to have the following distribution: caught on 0.85 mm mesh, 17.2%; on 0.425 mm mesh, 63.6%; on 0.250 mm mesh, 16.7% and on 0.150 mm mesh 2.5%. In another experiment a polymer mixture of 10% PVOH (25K MW), 20% alumina, 0.1% protease peptone #3 with a viscosity of 48.8 cps was sprayed with a pressure of 11 psig on the reservoir and 6 slpm of sweep gas. Beads from this run were: 1% on 0.85 mm, 1.8% on 0.425 mm, 32% on 0.25 mm, 40% on 0.125 mm, 18% on 0.075 mm and 8% less than 0.075 mm.

Doping PVOH Beads with Other Polymers

A polymer mix consisting of 5% PVOH (78K MW), 1.5 PVOH (125K MW), 3.5% PVOH (10K MW), 0.1% protease peptone #3, 0.05M $Na_2HPO_4$ and 20% alumina was made.

This polymer composition was divided into four 120 gram batches to which was added the following: To batch 1) 2 g of PVP (40K MW); to batch 2) 4 g of PVP (40K MW); to batch 3) 6 gm of PVP (40K MW); and to batch 4) 2 g of PEG8000. Beads were made from these mixtures and compared with beads made with no added polymers in terms of their stability in water. Beads were placed on a glass slide, examined under a stereo microscope at 20× and then a drop of water was added and the dissolution, if any was observed. Batch 1 dissolved more quickly than the undoped beads. Batch 2 and 3 dissolved slightly faster than batch 1 but the difference between 2 and 3 was not detectable. Batch 4 dissolved very quickly.

Encapsulation for Soil Delivery Using a Soybean Root Colonizing Bacteria

Cells (a strain of *Pseudomonas fluorescens* known to colonize soybean roots) are grown from a standardized inoculum ($5\times10^7$ cfu/ml) for 16 hours. Medium of choice is King's B with 50 μg/ml of rifampicin added. Use of a M9 minimal medium results in a drastic decrease in cell viability, as much as five logs following encapsulation. Cells are harvested by centrifugation and resuspended in a small amount of supernatant fluid. In most cases the volume of suspension fluid is determined such that it is preferably not more than 5% of the polymer solution volume although it may be as high as 20% without difficulty. Cells are mixed with a solution containing 10% (w/v) poly(vinyl alcohol) (M.W. 25,000, 98% hydrolyzed, 20% $Al_2O_3$, 0.1% Protease Peptone #3 (Difco Co.), and 1% dextrose. Immediately after mixing the solution is formed into beads by spraying from a spray nozzle into cold hexane. The beads thus formed are collected from the hexane and freeze dried. Cells viability in the polymer mix was $1.3\times10^{10}$ cfu/ml. After freeze-drying the beads viability was determined to be $1.3\times10^8$ cfu/ml. In a typical colonization assay, beads are used to inoculate soil "in furrow" in a pot at rate of 0.2 gram of beads per pot. Controls are cell-free beads (negative control) and liquid inoculum (positive control). Plants (Soybean Williams variety 79) are allowed to grow for two weeks and then the roots are harvested and rhizoplane is assayed for the colonizing bacteria. Results showed that there was no difference in colonization of the roots (as determined by Duncan's Multiple Range Test for Variable), between freshly grown liquid inoculum and encapsulated cells. Both colonized at levels of approximately $2\times10^5$ cfu/gm of root.

Encapsulation for Leaf Delivery Using a Leaf Colonizing Pseudomonad

Cells of a leaf colonizing pseudomonad were grown and harvested as previously described except two media were used, King's B (without rifampicin) and Nutrient Broth (Difco). Cells grown in the King's B were added to the polymer mix (10% (w/v) PVOH, 25,000 M.W.) at $9.5\times10^9$ cfu/ml and were present in the finished beads at a concentration of $2\times10^9$ cfu/ml. Cells grown in nutrient broth were mixed $5.5\times10^8$ cfu/ml in the polymer mix and were present in the finished beads at a concentration of $2.5\times10^7$ cfu/ml. These beads are suitable for delivery to the leaf surface in the following manner. The beads are suspended in a PVOH solution ranging in concentration from about 0.25-10% (w/v) and preferably from about 0.5% to 2% (w/v). The solution may contain other material adapted to enhance the adhesion of the beads to a particular leaf surface. The solution can be sprayed onto the leaf surfaces using conventional spray equipment.

Encapsulation of a *Bacillus sp* for Soil Delivery

A *Bacillus sp* having activity against corn root worm was grown in a 1% tryptone-1% glucose medium. Cells were inoculated using 20 ml of a 24 hr. old subculture for every 300 ml of medium. Cells were grown at 30° C. for 24 hours at 200 rpm. Cultures were harvested by centrifugation, resuspended in water and mixed with a prepared polymer mix to give final concentrations in the polymer mix of 10% PVP, 30% $Al_2O_3$ and 2% Protease Peptone #3. Dow Antifoam C (Dow Chemical, Midland, Mich.) was added to suppress foaming. Beads were made using a spray tip and spraying into hexane at $-30°$ C. Beads were collected from the hexane and freeze-dried. Beads were tested and found to contain $5\times10^9$ cfu/1.5 g of beads. Beads were broadcast onto pots in which corn had been planted. When corn was at an appropriate size corn-root worms were added and corn was allowed to grow. Analysis for damage was done by root weight (the less weight the more damage). Control was beads without cells at a rate of 1.5 g/pot. Beads were added at 1.5, 4.5 and 7.5 g/pot. Positive control was Furadan insecticide. Eight replicates were done on each treatment. Results showed the plants exposed to encapsulated cells had significantly higher root weights than the Furadan control when added at the 4.5 and 7.5 gm per pot rate.

Encapsulation of Bacillus thuringiensis var. Kurstaki

A 200 ml culture of B. t. var. kurstaki was reduced to a cell paste containing mostly spores and toxin crystals. This paste was resuspended to the original 200 ml volume using sterile water and 1 ml of this suspension was added to 100 ml of a 10% polyvinylalcohol solution. Beads were formed using the above polymer mix as previously described. These beads were tested for activity against tomato hornworm. One gram of beads was suspended in 10 ml of water and 0.05 ml of this solution was painted onto each of six tomato leaves. Leaves were placed in a petri dish with a piece of filter paper moistened with deionized water. Five larvae were added to each dish. A positive control consisted of unencapsulated B. t. used at the same concentration and a negative control of beads without spores or toxin crystals. The assay was read after four days. In the assay using beads without cells 27/30 larvae lived. This result indicates that the beads themselves were not toxic to the larvae and did not inhibit their feeding. In the assays with B. t. (both encapsulated and unencapsulated) all of the larvae died.

Encapsulation of a Fungus Alternaria cassiae

Figure 5:
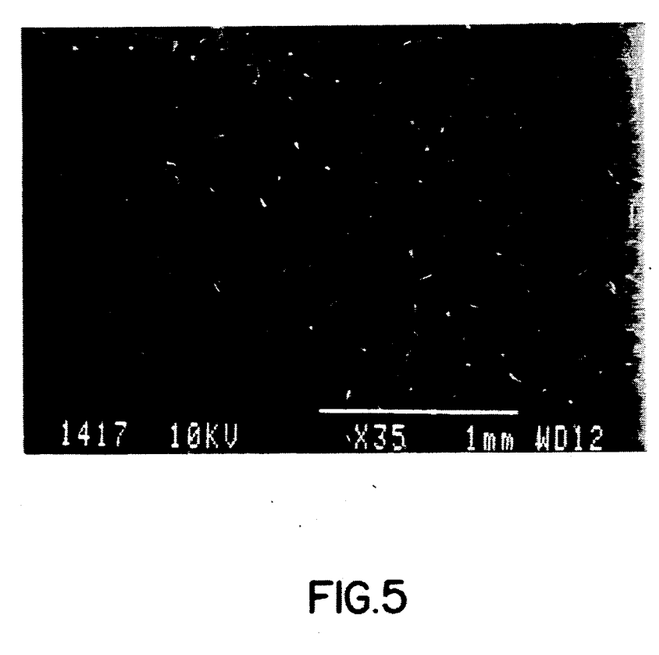
FIG. 5 represents PVOH beads adhering to a leaf surface after rain.

Starting material was conidia of Alternaria cassiae in the form of a dry powder. A 0.13 g sample was placed in a test tube with a surfactant in 6M sorbitol, mixed well to disperse the spores and allowed to stand for approximately one hour. This presoak slows the wetting of the spores when they are placed in the water-soluble polymer solution and enables them to withstand the freezing portion of the encapsulation process. Without this pretreatment all viability is lost. Pretreated spores were mixed with 5% polyvinyl alcohol solution and immediately sprayed into hexane at −30° C. to form beads. Beads are freeze-dried until just dry. Overdrying causes loss of viability. Viability of the encapsulated spores varies with the amount of drying and ranges between 20–90%. These beads are mixed with water or desired adjuvants and sprayed onto the surface of sicklepod leaves. Encapsulated spores have a slightly delayed germination and can survive a few hours longer when mixed with water which is an advantage when spraying plants in the field. Poly(vinyl alcohol) beads stick tenaciously to the leaf surface which renders them rainfast. Encapsulated spores are able to infect and kill sicklepod plants. Referring to FIG. 5, PVOH beads are shown adhering to the leaf surface of velvet-leaf even after flushing the leaf surface with water.

We claim:

1. A method for producing a viable biological material in the form of free flowing beads comprising the steps of:
    a) admixing a viable biological material having bound water with an aqueous nonionic polymer solution in which the polymer is present at a concentration of at least 3% w/v;
    b) forming a plurality of polymeric by spraying the resulting mixture of Step a) into a circulating water-immiscible nonsolvent for said polymer, said nonsolvent being maintained at a temperature sufficient to freeze the beads but not so low as to cause freeze fracture of the beads;
    c) recovering the frozen beads of Step b) under conditions wherein the beads are kept frozen; and
    d) drying the frozen beads of Step c) until essentially all unbound water is removed whereby a water level is provided sufficiently low to prevent clumping and loss of bead integrity but sufficiently high to maintain the viability of the biological material.

2. The process of claim 1 wherein the dried beads contain 1–2 weight percent water.

3. The method of claim 1 wherein the polymer solution contain a densification agent.

4. The method of claim 3 in which the densification agent is alumina.

5. The method of claim 1 in which the polymer is poly(vinyl alcohol).

6. The method of claim 1 in which the polymer is polyvinylpyrollidone.

7. The method of claim 1 in which the polymer is dextran.

8. The method of claim 1 in which the polymer is derivatized cellulose.

9. The method of claim 1 in which the biological material is a microbe.

10. The method of claim 9 in which the microbe is a bacteria.

11. The method of claim 9 in which the microbe is a fungus is pretreated to delay wetting during the encapsulation.

12. The method of claim 10 in which the bacteria is a strain of Bacillus thuringiensis.

13. The method of claim 10 in which the bacteria is a Pseudomonas sp.

14. The method of claim 11 in which the fungus is Alxernaria cassiae.

15. The product produced in accordance with the process of claim 1.

16. A method for producing an encapsulated protein or peptide in the form of free flowing beads comprising the steps of:
    a) admixing a protein or peptide with an aqueous nonionic polymer solution in which the polymer is present at a concentration of at least 3% w/v;
    b) forming polymeric beads by spraying the resulting mixture of Step a) into a circulating water-immiscible nonsolvent for said polymer, said nonsolvent being maintained at a temperature sufficient to freeze the beads but not so low as to cause freeze fracture of the beads;
    c) recovering the frozen beads of Step b) under conditions wherein the beads are kept frozen; and
    d) drying the frozen beads of Step c) to a water content of about 1–2 weight percent.

17. The method of claim 16 wherein the polymer solution contains a densification agent.

18. The method of claim 17 in which the densification agent is alumina.

19. The method of claim 16 in which the polymer is poly(vinyl alcohol).

20. The method of claim 16 in which the polymer is polyvinylpyrollidone.

21. The method of claim 16 in which the polymer is dextran.

22. The method of claim 16 in which the polymer is derivatized cellulose.

23. The product produced in accordance with claim 16.

* * * * *